United States Patent
Hartley

(10) Patent No.: US 6,610,986 B2
(45) Date of Patent: Aug. 26, 2003

(54) SOFT IONIZATION DEVICE AND APPLICATIONS THEREOF

(75) Inventor: Frank T. Hartley, Arcadia, CA (US)

(73) Assignee: Ionfinity LLC, Altadena, CA (US)

( * ) Notice: Subject to any disclaimer, the term of this patent is extended or adjusted under 35 U.S.C. 154(b) by 0 days.

(21) Appl. No.: 10/180,448

(22) Filed: Jun. 25, 2002

(65) Prior Publication Data

US 2003/0136918 A1 Jul. 24, 2003

Related U.S. Application Data

(60) Provisional application No. 60/347,685, filed on Jan. 8, 2002, and provisional application No. 60/336,841, filed on Oct. 31, 2001.

(51) Int. Cl.$^7$ .................................. H01J 27/00
(52) U.S. Cl. ............... 250/423 R; 250/382; 250/286; 250/287
(58) Field of Search ............... 250/423 R, 382, 250/287, 286

(56) References Cited

U.S. PATENT DOCUMENTS

| | | |
|---|---|---|
| 3,147,445 A | 9/1964 | Wuerker |
| 3,947,716 A | 3/1976 | Fraser |
| 3,970,887 A | 7/1976 | Smith |
| 4,027,165 A | 5/1977 | Jacobs |
| 4,307,507 A | 12/1981 | Gray |
| 4,311,669 A | 6/1982 | Spangler |
| 4,685,996 A | 8/1987 | Busta |
| 4,855,636 A | 8/1989 | Busta |
| 4,857,799 A | 8/1989 | Spindt |
| 4,926,056 A | 5/1990 | Spindt |
| 4,964,946 A | 10/1990 | Gray |
| 5,505,343 A | 1/1991 | Knickerbocker |
| 5,192,865 A | 3/1993 | Zhu |
| 5,493,115 A | 2/1996 | Dienzer |
| 5,614,072 A | 3/1997 | Vigh |
| 5,668,373 A | 9/1997 | Robbat |
| 5,672,868 A | 9/1997 | Mordehai |
| 5,726,076 A | 3/1998 | Tasker et al. |
| 5,726,448 A | 3/1998 | Smith |
| 5,736,739 A | 4/1998 | Uber |
| 5,738,774 A | 4/1998 | Harrison |
| 5,811,820 A * | 9/1998 | Kirchner et al. ........ 250/423 R |
| 5,879,949 A | 3/1999 | Cole et al. |
| 5,909,086 A | 6/1999 | Kim et al. |
| 5,952,652 A | 9/1999 | Taylor |
| 5,962,288 A | 10/1999 | Aksenov et al. |
| 6,051,378 A | 4/2000 | Monforte |
| 6,060,327 A | 5/2000 | Keen |
| 6,100,521 A | 8/2000 | Doring |
| 6,159,686 A | 12/2000 | Kardos et al. |
| 6,289,242 B1 | 9/2001 | Phipps |
| 6,323,482 B1 | 11/2001 | Clemmer |

* cited by examiner

Primary Examiner—John R. Lee
Assistant Examiner—Zia R. Hashmi
(74) Attorney, Agent, or Firm—Carl A. Kukkonen, III

(57) ABSTRACT

A soft ionization device is disclosed that comprises a series of electrodes having pacing less than the means free path of the molecules to be ionized. In some embodiments, the soft ionization device is used in various applications that require ion or electron sources such as biological or chemical reactors, ion milling, and numerous replacements for conventional hot cathode systems. In another embodiment, a valence spectrometer is disclosed that is configured to variably ionize molecules by their valiancy. In other embodiments, the ionization device is coupled to a spectrometer for the characterization of biological matter. Also disclosed is a preconditioner for preparing biological matter to be ionized.

25 Claims, 4 Drawing Sheets

SOFT IONIZATION DEVICE AND APPLICATIONS THEREOF

CROSS-REFERENCE TO RELATED APPLICATIONS

This application claims benefit of U.S. Provisional Application No.: 60/336,841 filed on Oct. 31, 2001, and U.S. Provisional Application No. 60/347,685 filed on Jan. 8, 2002, both of which are hereby fully incorporated by reference.

BACKGROUND OF THE INVENTION

Ionization of gaseous molecules is conventionally initiated by photon bombardment, charged particle impact, ultraviolet radioactive ionization, or by thermal electron beams. Such ionization techniques are typically utilized for mass spectrometers and ion mobility spectrometers. During ionization, depending on the level of impact energy, one of two events occur, either electrons are ejected from atoms and molecules or the molecules themselves are fractured into complement of fragments with diverse charge states. These processes are known as hard ionization and while they can be utilized to provide a measurement indicative of the atoms and molecules contained within the ionized sample, many components cannot be measured. Further, these 'hard' ionization mechanisms are inefficient with approximately 0.1% of atoms or molecules ionized. In addition, conventional mass spectrometers require low pressure ("hard vacuum") to operate to prevent higher velocity ions from colliding with a slower moving atoms and molecules (thermal velocities) that, during passage through the spectrometer, attenuate ion currents below detectable limits.

Figure 1:
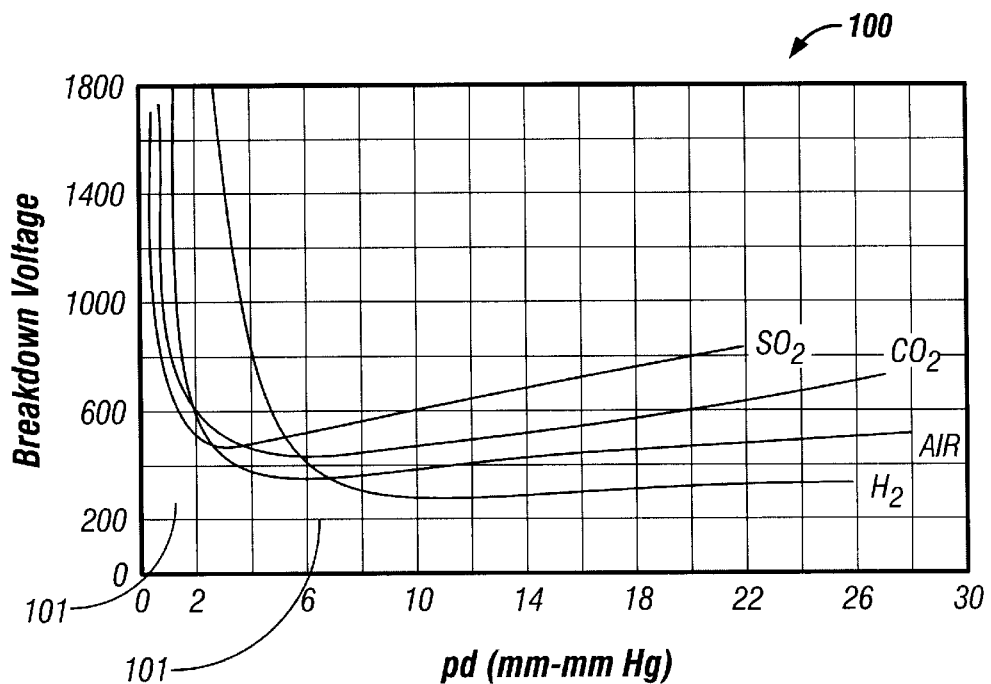
Figure 2A:
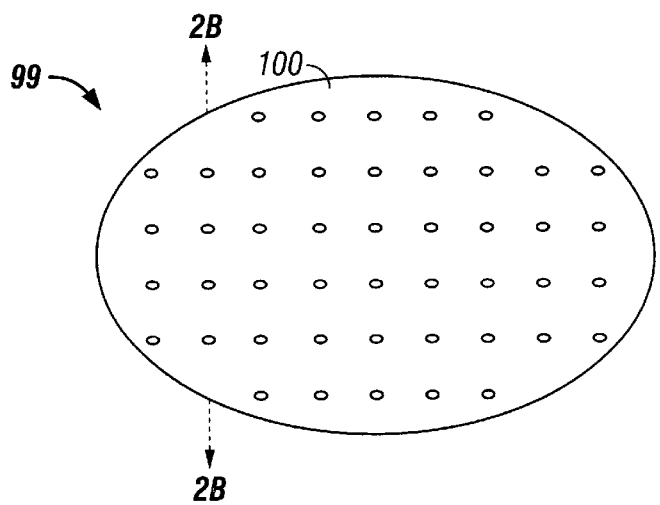
Figure 2B:
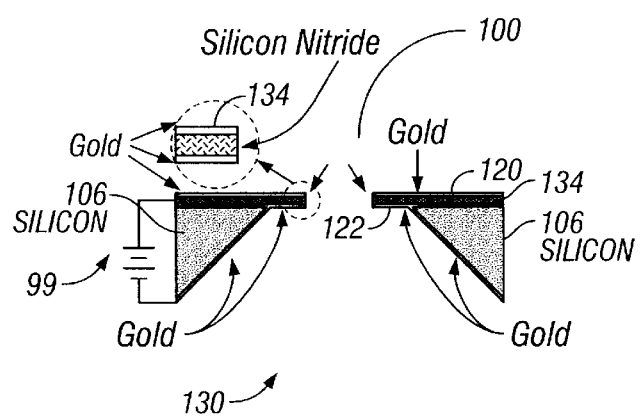

Moreover, conventional systems for ionization are susceptible to avalanche arcing when gases ionize in high electric fields. This phenomenon results because the mean free path length between molecules (at the relevant gas pressure) is greater than the electrode separation within the ionization device (empirical measurements showing the breakdown voltage versus gas pressure are identified in the Paschen curve of FIG. 1). If conventional systems could be configured to operate under the Paschen curve, then ionization would occur without avalanche arcing.

Current ionization systems coupled to detection systems are unable to characterize a wide range of biological matter. This is due in part because most biological matter comprises complex molecular structures that are susceptible to fracture, thus making it hard to characterize. In addition, some biological matter such as bacteria have varying masses depending on the stage of replication. Accordingly, as conventional techniques necessarily fracture the biological matter, users are forced to examine a spectrum of mass data corresponding to the various atoms and molecules that made up the examined matter rather than the overall mass of the biological matter.

In addition, there are many applications that utilize an ion or electron source that would benefit from a low cost efficient replacement such as field emission cathodes coated with low effective work-function materials. However, such cathodes are difficult and costly to manufacture and often have wide range of emissions and so there remains a need for an improved electron source.

It will be appreciated that there are other applications that are desirable for ionization including the characterization of ions by their valiancy, if an ionization system were sufficiently "soft", efficient, small and inexpensive, and it is to this end that other aspects of the invention are directed.

SUMMARY OF THE INVENTION

The invention is disclosed in a robust, efficient, temperature-insensitive, compact, and easy to manufacture ionizing device with a substrate having at least one opening. The substrate includes a first conductive electrode on a first surface and a second conductive electrode extending on a second surface that are separated by an insulating element to form an opening between the electrodes the width of the insulator. Preferably, the thickness of the insulating element is less than 1 micron. In some embodiments, the ionizing device is coupled to a detection system to characterize genetic material such as deoxyribonucleic acid (DNA), ribonucleic acid (RNA) and proteins for use in fields such as proteomics, drug discovery, diagnostics, identification of genetic material, metabolomics, and forensics. In addition, the detector elements within the detection system may be configured to collect detected genetic material so that they may later be blotted onto nitrocellulose paper.

In another embodiment, a system for producing ions and electrons is disclosed. This system includes an ionizing membrane having a thick supporting portion with pores formed therein. Like the ionizing device, the membrane has first and second metal electrodes coated on surfaces of the thick supporting portion extending into the pores. The distance between the first and second metal electrodes within the pores of the thick supporting portion is less than the mean free path of a molecule being ionized so that molecules ionized by the pore will be subject to secondary collision and thus fracture. A field generating element is also used for directing the ions and electrons produced by the ionizing membrane. The ions created by the system may be utilized for any application requiring a source of ions such as ion focused milling, maskless ion implantation, ion beam lithography, semiconductor mask modification, semiconductor chip wiring modifications, and ion mass spectrometry, as well as the supply of pure species for chemical reactors and biological reactors. Furthermore, as ions are produced, electrons are also "stripped" from the molecules which are directed by the field generating element for use with applications such as discharge light sources, flat panel displays, thyratrons, microwave switches, diodes, triodes, tetrodes, pentodes, and other replacements for hot-cathodes.

In another embodiment, a valence spectrometer is disclosed that is configured to incrementally increase an ionization field so that all molecules with a valence level equal or below the ionization field strength will be ionized. Like the embodiments above, the system incorporates an ionizing device as described above that is configured to ionize molecules passing therethrough below a specific valence level. A detection element coupled to said ionizing device determines the number of ionized molecules.

Also disclosed is a system for ionizing multiple samples in parallel comprising an ionization membrane as described above with an array of pores. Coupled to the ionization membrane are a plurality of inlets configured to supply each sample to a single pore on the ionizing membrane. In addition, each pore may have one or more detector elements aligned thereto and configured to detect the passage of ions through the pores to a specified location (thereby providing measurements analogous to an ion mobility spectrometer). The current detected on the detector elements is proportional to the concentration of matter on such elements and can be used for quantitation measurements.

As many difficulties arise when ionizing a sample of biological matter, a technique is disclosed (which may be used alone or in combination with an ion characterization system) for ultrasonically resonating a sample to remove materials that either confuse or are not instructive for characterizing the constituents of the biological matter. The technique utilizes a system includes a tubular member configured to receive liquid samples having biological matter suspended therein. A piezoelectric generator is circumferentially coupled to the tubular member so that it may ultrasonically resonate the contents of the tubular member to remove undesirable matter. The resulting liquid is delivered to a vaporizer that vaporizes the liquid prior to ionization.

Also disclosed are a soft ionization device and ion characterization system for the characterization of nuclear, biological and chemical threats as well as a technique for generating a unipolar plasma.

BRIEF DESCRIPTION OF THE DRAWINGS

The features, objects, and advantages of the invention will become more apparent from the detailed description set forth below when taken in conjunction with the drawings in which like reference characters identify correspondingly throughout and wherein:

FIG. 1 illustrates a Paschen curves for various gases;

FIGS. 2A–2B illustrates a soft ionization device of the present system, with FIG. 2*b* showing a cross-section along the line 2B—2B in FIG. 2A;

FIG. 3 illustrates a cross section with details of the electric fields of the soft ionization device of FIGS. 2A–2B;

FIG. 4 illustrates an ion array mobility spectrometer utilizing the soft ionization device of FIGS. 2A–2B;

FIG. 4 illustrates a valence spectrometer utilizing the soft ionization device of FIGS. 2A–2B;

FIG. 5 illustrates a cross section of a parallel ion mobility spectrometer utilizing the soft ionization device 99 of FIGS. 2A–2B wherein each pore has a separate lane of detectors corresponding thereto; and FIG. 6 illustrates a preconditioner configured to pretreat biological matter for ionization and characterization by a spectrometer utilizing the soft ionization device of FIGS. 2A–2B.

DESCRIPTION OF THE EXEMPLARY EMBODIMENTS

With reference to the remaining figures, exemplary embodiments of the invention will now be described. The current invention is embodied in a soft ionization device and various applications thereof. While the invention is primarily detailed in connection with the several embodiments herein, it will be appreciated by one of ordinary skill in the art that the invention may be used for a variety of applications where it is desirable to have an efficient ionization source as the current invention provides a technique where the “mean free path” between molecules to be ionized is greater than electrode separation so that only ionization occurs.

With reference to FIG. 1, a Paschen curve 100 for various gases is illustrated. This curve represents the breakdown voltage of the gases at various characteristic points. On the left side and under each Paschen curve, generally in the area 101, ionization of the gas occurs using the special membrane described herein, to render the gases to operate in this location.

The current invention provides a “soft” ionization technique is as it ionizes without fragmenting the molecular structure that is not susceptible to temperature variations. This arrangement allows large organic compounds to be analyzed without breaking them into smaller atomic fragments.

Details of the membrane are illustrated in FIG. 2B, shows a cross sections of the membrane of FIG. 2A. The miniature soft ionization device 99 is formed by micromachining one or more small pores 100 (referred to herein as an array) through a relatively thin membrane 105. The membrane 105 may be, for example, of sub micron thickness. The material 106 of the substrate itself may be silicon or any other easy-to-machine material. Metal electrodes 120,122 are located on respective sides of the membrane 100. The metal can be any material such as chrome or titanium or gold.

In formation of the soft ionziation device 99, a plurality of pores such as 130 are formed from the bottom 132. The pores may generally taper as shown towards the top portion of the pore 133 (for example, if the pore feature is generated using photolithography, each pore may etched to form a pyramid-like shape with the sides of the pyramid projecting tapering at an angle of approximately 55°). The top portion of the pore 133 may have a dimension 136 which may be, for example, 2 to 3 microns. An opening may be formed in the top metal coating 120, with the same sized opening being formed in the bottom metal coating 122. For example, the pore may be formed by focused ion-beam milling (a maskless process).

The substrate material 106 also includes a dielectric layer 134. The thickness 136 of the dielectric layer sets the distance between the metal electrodes 120 and 122. The dielectric thickness can be to 200–300 nm, and the dielectric can be for example, silicon nitride, alumina, or any other similar material. The important feature of the material is its dielectric breakdown. The dielectric can in fact be thinner than 200 nm, in fact can be any thickness, with thicknesses of 50 nm being possible.

Preferably, the distance between the electrodes 120, 122 is less than 1 micron. When this small separation is maintained, electric field strengths on the range of mega volts per meter are produced for each volt of potential difference between the electrodes 120, 122.

One of ordinary skill in the art will appreciate that membranes are preferably not formed simply from the thin, sub micron elements. Membranes that are formed in this manner are often too fragile to sustain a pressure difference across the membrane, or to survive a minor mechanical shock. In the current embodiment, the thicker supporting substrate part 105 is used, and is back-etched through to the membrane. By forming the substrate in this manner with relatively thick substrate portions 105, 106, separated by back-etched pores 100, the structure of the device can be maintained with relatively small distance between the electrodes.

In another embodiment the soft ionization device of the current invention is utilized to generate ions and electrons. As shown in FIG. 3, neutral charged molecules 301 are ionized by electric fields (illustrated as 303) generated by the soft ionizing device 99. Electrons 305 are stripped from the neutral charged molecules to form ions 307—with the electrons and ions being dispersed according to their charge. It will be appreciated that this arrangement may be used as an efficient source of electrons or ions. For example, this ion source may be used for applications such as ion focused milling, maskless ion implantation, ion beam lithography, semiconductor mask modification, semiconductor chip wiring modification, and ion mass spectrometry. In addition, the current soft ionization device may be utilized in situations where it is desirable to have a pure source of molecules, and so desired molecules may be dispersed by mass charge for supply to a chemical or biological reactor. This embodiment may also be modified so that the electric field diverts and directs electrons to a predetermined location. Such an electron source can act as a replacement for conventional electron sources such as thermionic emission cathodes (hot-cathodes) treated with low-work-function materials. In particular, the soft ionization device may be used to generate electrons within a variety of gas discharge light sources (such as fluorescent bulbs), thyratrons, microwave switches, low pressure diodes, triodes, tetrodes or pentodes.

Another embodiment utilizes the ionization technique described herein to form a valence spectrometer that may be used in connection with a mass spectrometer or other instrument unable to differentiate molecules of similar mass/charge. The valence spectrometer incorporates a soft ionization device that is configured to generate ionization fields that can be incrementally increased over small intervals to permit differentiation of molecules having similar masses but with different valence states (through an ion current measurement from a Faraday Cup placed adjacent to the soft ionization device or through electron current measurement from an anode placed adjacent to the soft ionization device). For example, the molecules CO and N have similar masses but their valence states are 14.014 and 15.581 eV respectively. First, the user may choose to apply a field of 14.013 eV across the soft ionization device to ionize all molecules having a valence state of 14.013 eV or less (as the spectrometer cannot differentiate what is detected by the Faraday Cup). Next, the user would adjust the field to 14.014 eV to determine the amount of CO in the sample. This process is then repeated at the appropriate ionization field strengths (first at 15.580 and second at 15.581) to determine the amount of N in the sample. As the valence spectrometer only requires a soft ionization device and either a cathode (such as a Faraday Cup) or an anode, the size of this device may be less than 1 mm by 1 mm.

Yet another use of the soft ionization device is to generate a uni-polar (or primary ionized) plasma, provided that the field strength across the membrane is sufficiently high and the system is closed. Once generated and after an initial start up period where the plasma will collide with neutral molecules until they are swept out of the system, the plasma may be pumped by an accelerating electric (or magnetic) field and deflected by translational or rotational fields with the electrons being collected by a Faraday Cup. Unlike conventional systems that operate under millitorr level vacuum where molecules are still subject to collision, the molecules within the unipolar plasma described herein include fewer slow moving (verses dominant proportion) neutral target molecules to collide with faster traveling ions nor does are there free electrons to neutralize ions (in fact, the unipolar ions repel each other further reducing the likelihood of collision). In addition, a system that generates unipolar plasma may also include a series of detection elements that are able to characterize the masses of all molecules contained with the plasma to determine relative concentrations. Accordingly, unlike previous systems that suffer from hard ionization effects and secondary ionization, the current system provides plasma substantially free of electrons or other differentially ionized molecules.

Figure 4:
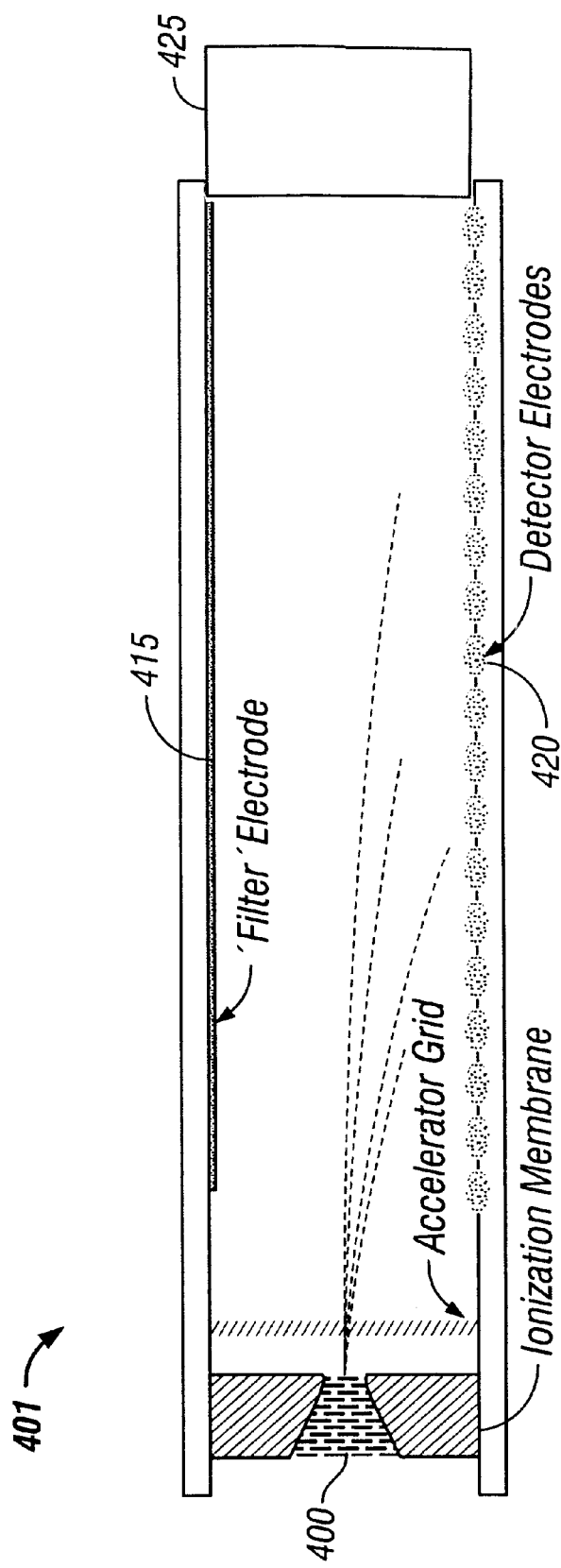

One application of the soft ionization device is for use in a miniature ion mobility spectrometer 401 as shown in FIG. 4. Conventional ion mobility spectrometers use a shutter gate to provide short pulses of ions. The shortened pulses of ions are often limited to about 1 percent of the total number of ions that are available for detection. However, resolution of such a device is related to the width of the ion pulse. The width of the ion pulse cannot be increased without correspondingly decreasing the resolution.

In the improved system of FIG. 4, total and continuous ionization of sample gas and continuous introduction of all ions into the chamber is enabled. Sample gases are introduced as 400 into the soft ionization device 405 of the type described above. In general, the soft ionization device 405 could include either a single pore device or could have multiple pores within the device.

Ions 410 from the membrane exit the membrane as an ion stream. Electrons in contrast move back behind (that is, to the other side of) the membrane, and further contribute to the ionization of the incoming gases. The atoms or molecules are carried through the body of the spectrometer by a gas feed system 425. The gas feed system includes either an upstream carrier gas supply and Venturi sampler, or a downstream peristaltic pump.

The ions are drawn towards the filter electrode 415 which receive alternating and/or swept DC electric fields, for the transverse dispersal of the ions. A repetitive ramping of the DC fields sweeps through the spectrum of ion species.

An important feature of this ion mobility spectrometer 401 is the high field strengths that can be obtained. At moderate ionization field strengths, for example <100,000 volts per meter, the mobility of ions at atmospheric and moderate pressures is constant. However, at higher ionization field strengths, such as 2 million volts per meter or greater, the mobility of the ions is nonlinear. The mobility changes differentially for high and low mobility ions. This change may be, for example, by 20 percent. Therefore, by applying a waveform that is formed of a short high-voltage and a long low or negative voltage to the filter electrodes, the ion species is disbursed between the filter electrodes. This waveform may be selected to provide a zero-time averaged field. In operation, the ions are transported laterally by a carrier gas stream. A low strength DC field may be supplied in opposition to the other field. This fields applied to the filter electrode may straighten the trajectory of specific ion species, allowing their passage through the filter. The other ion species collide with the electrodes. Sweeping of the DC field may facilitate detection of the complete ion spectrum.

An array of detector electrodes 420 are located downstream of the filter electrodes 415. The selected ions have straightened trajectories, and these filter electrodes deflect the straightened-trajectory ions into detection electrodes, where they are detected. The detected current provides a direct measure of the number of ions. The number of ions is effectively proportional to the vapor concentration.

This system generally operates as conventional ion mobility spectrometers but the soft ionization device (in connection with an ion mobility spectrometer and other types of spectrometers) allows for the sampling of the smallest possible ion masses (hydrogen having a mass of one atomic mass unit) to large fragments with masses greater than 10,000 AMU. For example, a soft ionization device in combination with an ion characterization system may characterize aqueous suspended proteins, RNA and ssDNA of around 500 kbases, and DNA of around 250 kbase-pairs as well as biopolymers, sugar chains, and drug compounds (all of which are not subject to fracture or decomposition using the soft ionization techniques disclosed herein) injected through a capillary nozzle into a low-pressure manifold where the suspended molecules, buffer complexes etc., are sublimated or vaporized into aerosol particles that are subsequently ionized during passage through the soft ionization device. The MW range of instrument is greater than $10^7$ (compared with <10 for gel electrophoresis), which accommodates all proteins (>mega Dalton capacity), RNA and ssDNA of around 500 kbases, and DNA of around 250 kbase-pairs. In addition, the invention disclosed herein may be implemented in parallel (as described in further detail below) such that thousands of species are concurrently processed in minutes as an analog to gel electrophoresis (compared to one hundred per day with gel electrophoresis and blotting), and are dispersed linearly with respect to mass and quantified with a resolution of better than 1 ng. Unlike conventional systems, no a priori DNA snippets or antigens are required to identify molecules.

Figure 5:
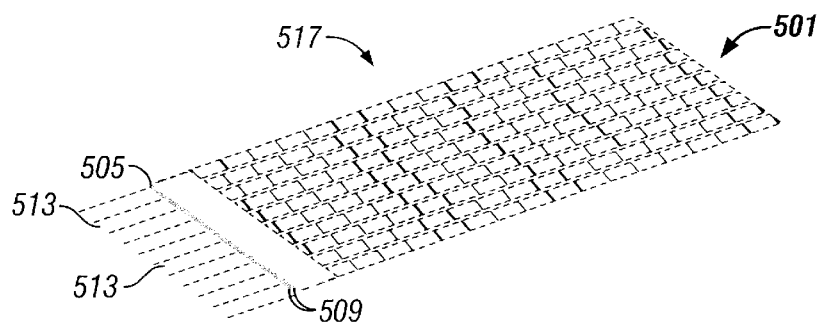

Forming the spectrometer in the manner described herein enables the system to be formed smaller, lighter, and with less cost than other devices of this type. This arrangement enables a wide range of applications; such as in situ biomedical sampling. One application is use of the miniature mass spectrometer is for metabolomics (the study of metabolomes) measurements. As there are no electron beam filaments and the like, any of the system components can operate at relatively higher pressures, for example pressures of 5 to 7 Torr or higher. With a Faraday Cup electrometer ion detector, sub-femtoamp levels of sensitivity may be obtained. Moreover, the device can be made relatively small and low-power. For example a complete system may weigh 1 kg and consume 10 watts. A sub-liter per second ion pump, or a membrane mechanical pump, can provide sufficient vacuum pumping. This system could be used as a portable device for finding various characteristics in exhaled breath, one technique for identifying metabolomes. For example, detection of carbon monoxide in exhaled breath may be used as a screening diagnostic for diabetes or for other conditions which have metabolic indicators Another embodiment shown in FIG. 5, provides for a parallel ion mobility spectrometer 501 with a soft ionization device 505 having a plurality of linearly spaced pores 509. Each pore is positioned along a lane comprised of an inlet 513 configured so that the sample input to each pore is segregated from the other pores. Each pore, in parallel, ionizes the sample fed therethrough which is then accelerated by an accelerator in the matter described above. A zero-time average dispersive field deflects the ionized sample onto an array of detector electrodes 517 having a series of rows where the ion current of the dispersed ionized samples are measured. Preferably, the detector electrodes are metal plates of two-dimensional CCD or APS modified matrix imagers.

The parallel ion mobility spectrometer may be used to perform parallel analyses, including applications analogous to electrophoresis. If desired for applications such as proteomics, the samples that contact and discharge on the filter electrodes may be blotted onto nitrocellulose paper for subsequent uncontaminated species 'cut-out' (via detector map). Alternatively, the spectrometer can disperse molecules over a conductive (electrical) sheet, a substitute for nitrocellulose paper blots, on which traditional radiological probing or staining could proceed. Furthermore, the spectrometer may incorporate micro-channel plates having integrated electrodes such that various mass molecules may be directly deposited thereon and quantized based on current. With these arrangements a spatial map is provided without the requirement tagging the desired samples with fluorescent, radioactive or other markers.

Figure 6:
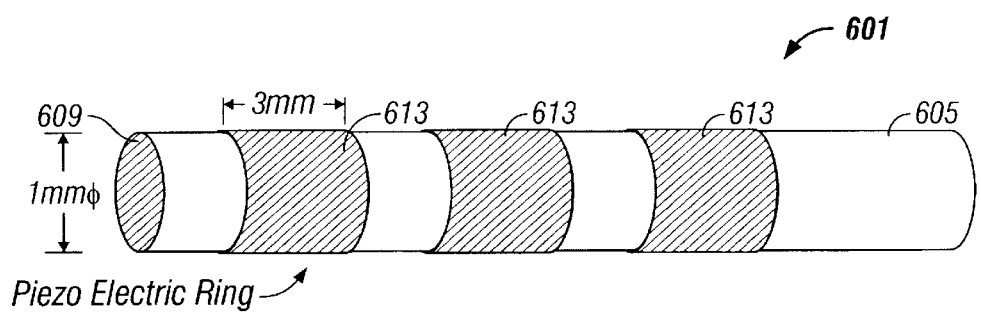
Figure 3:
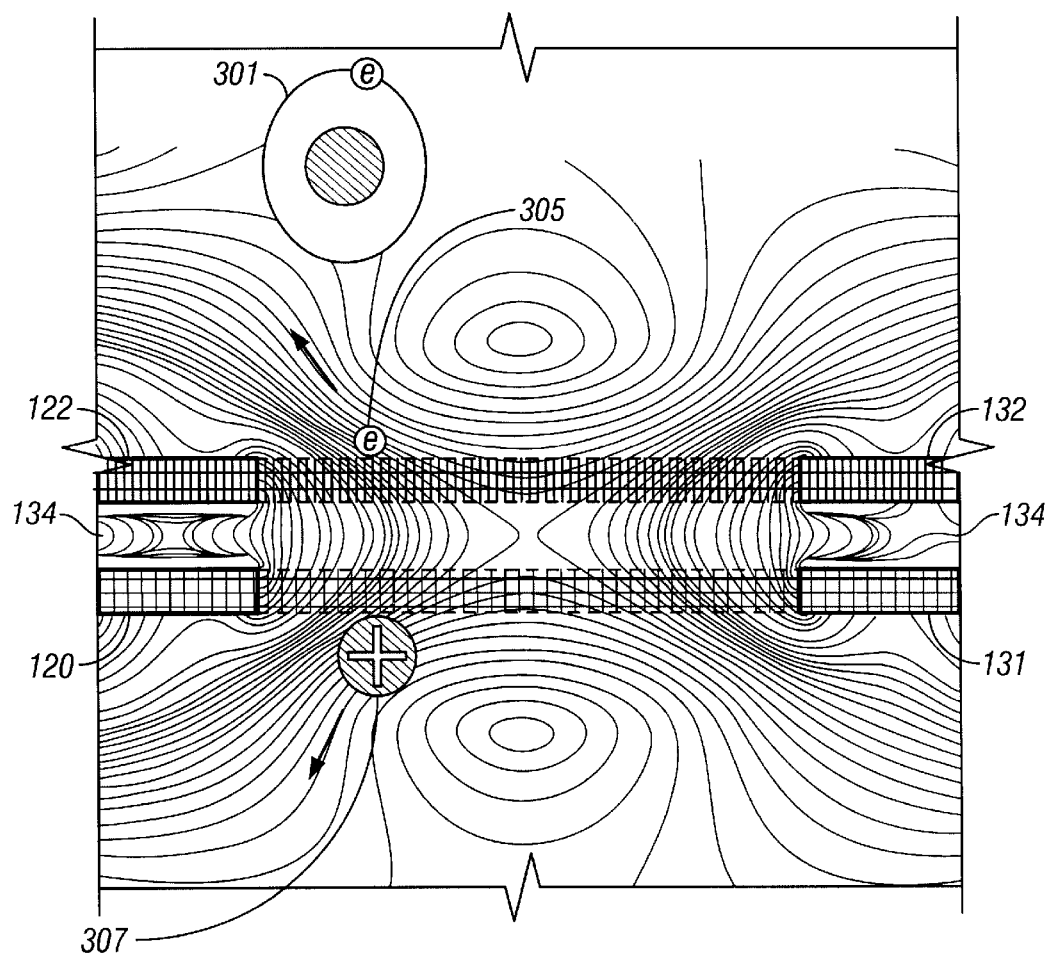

In yet another embodiment and as illustrated in FIG. 6, a preconditioner 601 is disclosed that may be used in connection with aspectrometer coupled to the soft ionization device disclosed above. The preconditioner provides a technique for pre-treating a sample to separate desirable matter from undesirable matter (such as proteins, wall debris and polysaccharides, etc.) before characterization by the mass spectrometer. The preconditioner comprises one or more tubes 605 in series, preferably made from titanium, having an inner annulus 609. Circumferentially coupled to the outer surface of the tube are one or more cylindrical piezoelectric generators 613 (rings) that generate ultrasonic frequencies up to and including 1 MHz. The diameter of the annulus is approximately 1 mm or such other size to correspond with the axial resonant cavity dimensions (for the aqueous suspended charge) of the piezoelectric generators.

In operation, the sample is suspended in a liquid such as deionized water and passed through the annulus 609 of the tube 605. This process is repeated, if needed, until the desirable matter (such as wpore proteins, DNA, lipids, and carbohydrates of a bacterium (virus)) is separated from the sample. This fluid is then vaporized in a low pressure manifold from where it is drawn into the soft ionization device and for detection by an ion characterization system (i.e., mass spectrometer, ion mobility spectrometer).

In some applications including anthrax detection, it is essential to remove the undesirable background material. The sensitivity of the ion characterization system must be sufficient to resolve these interactions and discriminate between the lowest concentration of BW and highest background concentration of background Bioaerosols. For example, the edema protein of anthrax has a molecular size of 92,477 amu while the anthrax toxin lethal factor precursor has a molecular size of 93,785 amu. In this range, the sampling system can distinguish molecular sizes as close as 10 amu. *B. subtilis* has a gyrA protein of 92,098 amu, difficult to distinguish by electrophoresis or chromatography, but easily separated by the sampling system. In addition, depending on the constituents of the sample, other pretreatment techniques, such as exposing the sample to warm deionized water (approximately 65° C.) may be utilized prior to the preconditioner.

The exemplary embodiments have been primarily described with reference to figures illustrating pertinent components of the embodiments. It should be appreciated that not all components of a complete implementation of a practical system are necessarily illustrated or described in detail, nor are all of the varying component layout schema described. For example, the soft ionization device may be used for a variety of applications requiring precise characterization of a large range of molecular weights such as a nuclear/chemical/biological agent detection system and for forensics. In addition, it will be recognized that the soft ionization device disclosed herein may be used in connection with a wide variety of ion characterization systems including: quadropole mass spectrometers, magnetic sector mass spectrometer, and ion mobility spectrometers. Accordingly, only those components and architectures necessary for a thorough understanding of the invention have been illustrated and described in detail. Actual implementations may contain more components or, depending upon the implementation, fewer components. Modifications to the preferred embodiments will be apparent to those skilled in the art. Consequently, the scope of the present invention should not be limited by the particular embodiments discussed above, but should be defined only by the claims set forth below and equivalents thereof.

What is claimed is:

1. A system, comprising:

an ionizing device, comprising a substrate having at least one opening, a first conductive electrode extending on a first surface of said substrate and a second conductive electrode extending on a second surface of said substrate, and an insulating element separating said first and second conductive electrodes at said at least one opening, wherein said first and second conductive electrodes are separated by a width of said insulating element; and a detection system coupled to said ionizing device for characterizing genetic material.

2. The system of claim 1 wherein the genetic sample is chosen from the group comprised of: deoxyribonucleic acid (DNA), ribonucleic acid (RNA) and proteins.

3. The system of claim 1 wherein the characterization of genetic material is utilized for one of the applications selected from the group comprised of: proteomics, drug discovery, diagnostics, identification of genetic material, metabolomics, forensics.

4. A system for producing ions and electrons, comprising:

an ionizing membrane having a thick supporting portion with pores formed in the thick supporting portion and having first and second metal eletrodes coated on surfaces of the thick supporting portion extending into the pores in the thick supporting portion, where a distance between the first and second metal electrodes within the pores of the thick supporting portion is less than the mean free path of a molecule being ionized; and a field generating element coupled to said ionizing membrane for directing the ions and electrons produced by said ionizing membrane.

5. The system of claim 4 further comprising a detection system coupled to said ionizing membrane for characterizing the ions produced by the system.

6. The system of claim 5, wherein the detection system is a spectrometer.

7. The system of claim 6, wherein the spectrometer is chosen from the group comprised of ion mobility spectrometers, mass spectrometers.

8. The system of claim 4 wherein the distance between the first and second metal electrodes within the pores of the thick supporting portion is less than or equal to one micron.

9. The system of claim 8 wherein the distance between the first and second metal electrodes within the pores of the thick supporting portion is in the approximate range of 200 nm to 300 nm.

10. The system of claim 8 wherein the distance between the first and second metal electrodes within the pores of the thick supporting portion is approximately 50 nm.

11. The system of claim 1 further comprising a field generating element for directing ions and electrons produced by said ionizing device.

12. The system of claim 1, wherein the detection system comprises one or more detector elements that are configured to neutralize and capture ions.

13. The system of claim 1, wherein the detection system is a spectrometer.

14. The system of claim 13, wherein the spectrometer is chosen from the group comprising: ion mobility spectrometers or mass spectrometers.

15. The system of claim 1 wherein the width of said insulating element is less than or equal to one micron.

16. The system of claim 15 wherein the width of said insulating element is in the approximate range of 200 nm to 300 nm.

17. The system of claim 15 wherein the width of said insulating element is approximately 50 nm.

18. The system of claim 1 wherein the width of said insulating element is less than or equal to the mean free path of a material being ionized by said ionizing device.

19. A system for ionizing multiple samples in parallel comprising:

an ionizing membrane having a thick supporting portion with pores formed in the thick supporting portion and having first and second metal electrodes coated on surfaces of the thick supporting portion extending into the pores in the thick supporting portion, where a distance between the first and second metal electrodes within the pores of the thick supporting portion is less than the mean free path of a molecule being ionized; and a plurality of inlets segregating the pores and configured to supply a different sample to each segregated pore on said ionizing membrane.

20. The system of claim 19, further including an array of detector electrodes configured to characterize the ionized samples.

21. The system of claim 20, wherein the detector electrodes quantitate ions discharged thereon.

22. The system of claim 19, further including one or more detector elements aligned to each pore and configured to detect the passage of ions through each pore.

23. The system of claim 19, wherein the distance between the first and second metal electrodes within the pores of the thick supporting portion is less than or equal to one micron.

24. The system of claim 23 wherein the distance between the first and second metal electrodes within the pores of the thick supporting portion is in the approximate range of 200 nm to 300 nm.

25. The system of claim 23 wherein the distance between the first and second metal electrodes within the pores of the thick supporting portion is approximately 50 nm.

* * * * *